(12) United States Patent
Park et al.

(10) Patent No.: US 6,683,464 B2
(45) Date of Patent: Jan. 27, 2004

(54) STABILIZED CONDUCTIVITY SENSING SYSTEM

(75) Inventors: Kyong M. Park, Thousand Oaks, CA (US); Tony Tuong Nguyen, Northridge, CA (US)

(73) Assignee: Kavlico Corporation, Moorpark, CA (US)

( * ) Notice: Subject to any disclaimer, the term of this patent is extended or adjusted under 35 U.S.C. 154(b) by 138 days.

(21) Appl. No.: 10/087,315

(22) Filed: Mar. 1, 2002

(65) Prior Publication Data

US 2003/0164708 A1 Sep. 4, 2003

(51) Int. Cl.⁷ .............................................. G01R 27/08
(52) U.S. Cl. ........................ 324/706; 324/691; 324/443; 324/439
(58) Field of Search ........................ 73/862.628, 61.71; 324/691, 693, 698, 705, 706, 713, 720, 722, 725, 439, 443, 444, 451; 338/13, 27, 28, 38, 44

(56) References Cited

U.S. PATENT DOCUMENTS

| | | | |
|---|---|---|---|
| 2,505,072 A | 4/1950 | Sunstein | 324/725 |
| 2,824,283 A | 2/1958 | Ellison | 324/700 |
| 2,830,265 A | 4/1958 | Ellison | 324/706 |
| 2,887,652 A | 5/1959 | Bendayan et al. | 324/642 |
| 2,891,218 A | 6/1959 | Werts | 324/610 |
| 3,147,431 A | 9/1964 | Bennett et al. | 324/706 |
| 3,287,978 A | 11/1966 | Knudsen | 374/172 |
| 3,495,167 A | 2/1970 | Eckfeldt | 324/706 |
| 3,536,999 A | 10/1970 | Mandler et al. | 1/699 |
| 3,617,878 A | 11/1971 | Senour | 324/610 |
| 3,683,671 A | 8/1972 | Van Swaay | 73/25.03 |
| 3,699,559 A | 10/1972 | Bochinski | 324/701 |
| 3,932,849 A | 1/1976 | Welch | 340/586 |
| 3,936,737 A * | 2/1976 | Jefferies, Sr. | 324/700 |
| 4,135,392 A * | 1/1979 | Young | 73/862.635 |
| 4,146,834 A | 3/1979 | Maltby et al. | 324/610 |
| 4,468,864 A | 9/1984 | Westphal et al. | 33/366.14 |
| 5,357,189 A | 10/1994 | Egami | 324/120 |
| 5,610,343 A * | 3/1997 | Eger et al. | 73/862.628 |
| 5,734,269 A | 3/1998 | Sakai et al. | 1/706 |
| 5,804,978 A | 9/1998 | Scheerer et al. | 324/706 |

* cited by examiner

Primary Examiner—N. Le
Assistant Examiner—Vincent Q. Nguyen
(74) Attorney, Agent, or Firm—Oppenheimer Wolff & Donnelly LLP

(57) ABSTRACT

A stabilized fluid conductivity measurement system includes a threaded metal housing with an inner portion having two probes for contacting the fluid to be measured and having an outer portion in which electrical circuitry is mounted. The circuitry includes a balanced square wave generator providing excitation to a modified Wheatstone bridge, including first and second input excitation terminals, and first and second output terminals. Fixed resistances may be located in 3 arms of the Wheatstone bridge, and the fourth arm may have two resistances with an intermediate tap; and one of the two probes is connected to this tap while the other probe is connected to one of the input excitation points.

20 Claims, 3 Drawing Sheets

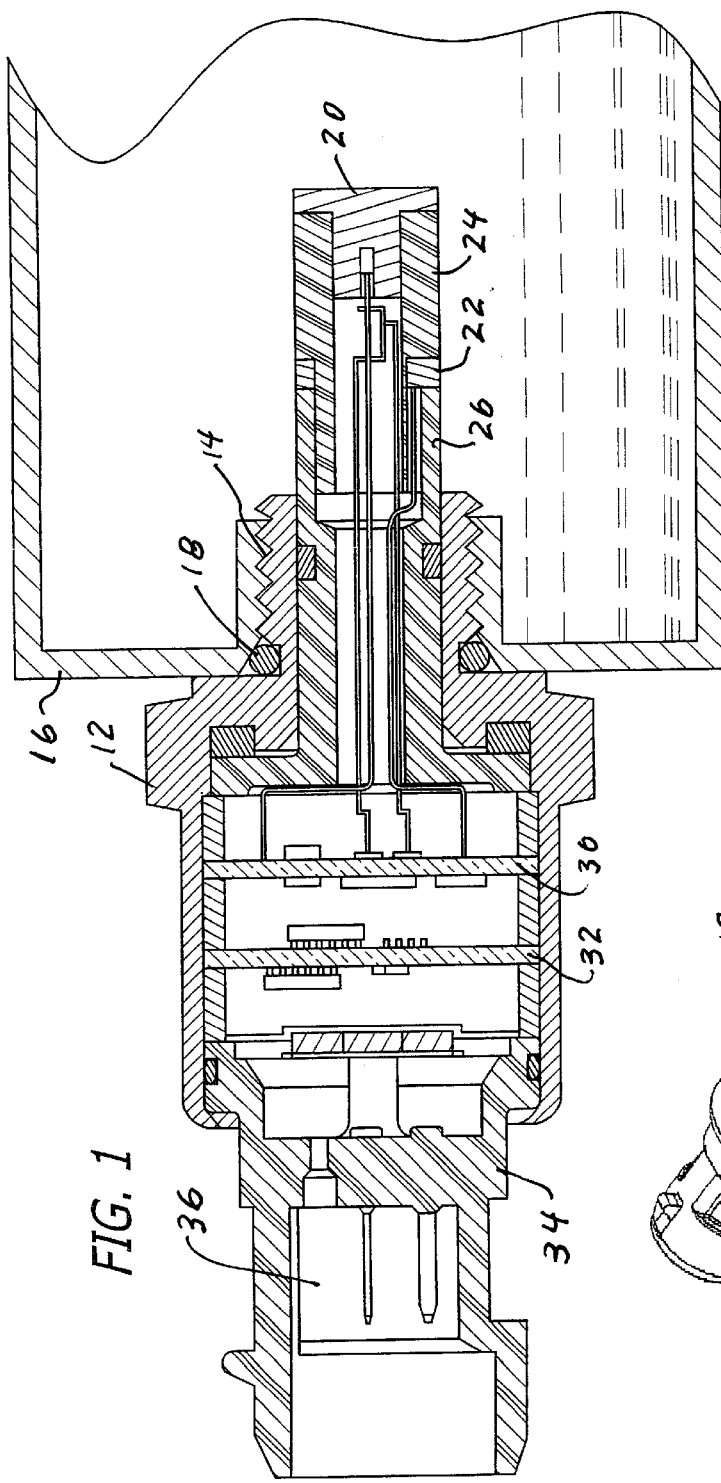
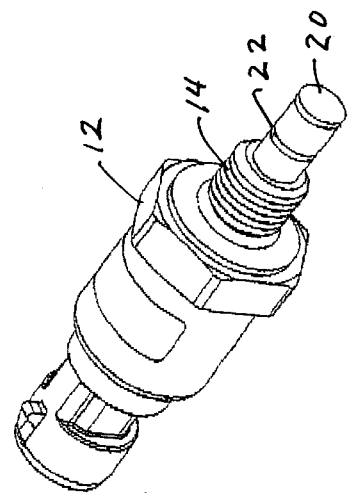
FIG. 1
FIG. 2

STABILIZED CONDUCTIVITY SENSING SYSTEM

BACKGROUND OF THE INVENTION

1. Field of the Invention

This invention relates to conductivity sensing systems, for detecting the varying conductivity, for example, of fluids.

2. General Background and State of the Art

In the measurement of the conductivity of fluids, such as distilled or de-ionized water, for example, it is known that the conductivity of the water is a function of impurities or contamination in the fluid or water. Efforts have been made to test the conductivity, but problems have arisen both with respect to short term, or momentary fluctuations of output readings, and also with regard to long term drift of the measured output. In the measurement of the conductivity of fluids, probes or electrodes normally extend into the fluids, and the resistance or conductivity is measured. When the resistance across the probes was employed in one arm of a Wheatstone bridge, and the bridge was energized with direct current, it was determined that (1) the short term variations in the output were so high as to make the determination of conductivity very difficult; and (2) there was a long term drift or shift in the output as a result of metal transfer or precipitation from one electrode to the other.

SUMMARY OF THE INVENTION

In order to overcome these problems, it has been determined that excitation with a square wave or alternating current signal with no net direct current flow, avoids the metal transfer and long term drift problems. Further, by using a modified Wheatstone bridge arrangement in which the probes are connected in parallel with resistors in the bridge, the short term fluctuations are substantially stabilized, and accurate output readings may be obtained.

In accordance with one preferred illustrative embodiment of the invention, a stabilized conductivity sensor has a threaded housing for securing into a container for the fluid to be measured, and two conductive metal probes are spaced apart and mounted on the inner portion of the housing. A Wheatstone bridge circuit is also mounted in the housing, and balanced square wave excitation to the bridge is provided. The Wheatstone bridge has resistors in all four arms of the bridge, and at least one of the arms of the Wheatstone bridge has a least two resistive portions with an intermediate tap. One of the probes is connected to this tap, and the other probe may be connected to one of the four terminals of the bridge. The output from the bridge is applied to a differential amplifier and then to a low pass filter to remove residual "noise" arising from the square wave combining function of the differential amplifier. The foregoing circuitry may be mounted in an upper portion of the housing which extends outside the fluid container.

In accordance with one preferred implementation of the invention, the Wheatstone bridge arrangement has first and second input excitation terminals, and first and second output terminals. Fixed resistors may be connected between the first input terminal and the first output terminal and between the first output terminal and the other second input terminal. A fixed resistance may extend between the first of the input terminals and the second output terminal, and two resistors with an intermediate tap may be connected between the second of the input terminals and the second output terminal. Finally, one of the probes may be connected to the tap between the two resistors, and the other probe may be connected to the first input terminal.

The resulting system avoids long term drift, and it stabilized so that it has minimal short term fluctuations.

Concerning the aspects of the construction, a first one of the probes may be mounted at the inner end of the housing, with the other probe being in a ring or sleeve configuration spaced back from and insulated from the first probe. The symmetrical configuration of the probes complements the circular geometry of the threaded housing. The circuitry may be positioned in an outer part of the housing extending outside of the container holding the fluid being measured.

Other objects, features and advantages of this invention will become apparent from a consideration of the following detailed description and from the accompanying drawings.

BRIEF DESCRIPTION OF THE DRAWINGS

FIG. 1 is a cross sectional view of a unit which is employed to measure the conductivity of a fluid, and wherein the unit including the circuitry mounted therein illustrates the principles of the invention;

FIG. 2 is perspective view of the unit of FIG. 1;

DETAILED DESCRIPTION OF THE PREFERRED EMBODIMENTS

Figure 3:
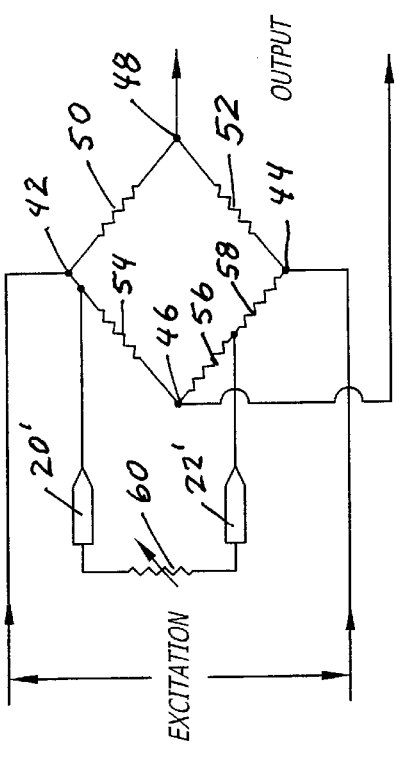
FIG. 3 represents a schematic electrical circuit indicating a specialized form of Wheatstone bridge which is utilized in a preferred embodiment of the invention.

While the specification describes particular embodiments of the present invention, those of ordinary skill can devise variations of the present invention without departing from the inventive concept.

Referring now to FIG. 1 of the drawings, the housing 12 includes a forwardly extending threaded portion 14 which is intended for threading into the wall 16 of a container having fluid therein, the conductivity of which is to be measured. An "O" ring seal 18 is provided for fluid tight sealing of the housing 12 to the container wall 16.

The conductivity of the fluid within the container 16 is measured by the resistance or conductivity between the probe 20 at the tip of the unit, and the second probe 22 which is a ring, spaced back from the probe 20. Both of the probes 20 and 22 are formed of conductive material such as stainless steel. The housing 12 is metallic, and can also be formed of stainless steel. The two sleeves 24 and 26 are of insulating material and may be of high strength plastic or may be formed of ceramic material. Circuit boards 30 and 32 are provided to receive signals from the probes 20 and 22 and to provide signal processing as will be described in greater detail hereinbelow.

An insulating housing 34 includes electrical connections 36 which provide power to the circuitry mounted on the circuit boards 30 and 32, and transmit the output signal indicating fluid conductivity to the user of the equipment.

In the present specification, both resistance and conductivity are discussed. Resistance is measured in ohms, and resistance is equal to the voltage applied to a circuit element divided by the current. Conductivity is the reciprocal of resistance, and is measured in terms of the basic unit of conductivity known as the "siemens". Previously the unit of conductivity was known as the "mho" which is the word "ohm" spelled backward. However, in recent years the term "siemens" has been used in place of the term "mho". The conductivity in siemens is equal to the current in amperes passing through the fluid or through a circuit element, divided by the applied voltage in volts.

Now, returning to the drawings, FIG. 3 shows a modified Wheatstone bridge circuit. A classical Wheatstone bridge circuit normally has two input terminals such as terminals 42 and 44 and two output terminals 46 and 48. On the right hand side of the Wheatstone bridge circuit as shown in FIG. 3, the two fixed resistances 50 and 52 are provided, between the input point 42 and the output point 48, for resistor 50; and between output point 48 and input point 44 for the fixed resistance 52. On the left hand side of the bridge we have a fixed resistor 54 between input point 42 and output 46; and two fixed resistors 56 and 58 are connected between the output point 46 and the input point 44. The two probes designated 20' and 22' are connected to point 42, and to the electrical connection between resistors 56 and 58, respectively. The variable resistance between probes 20' and 22' is indicated schematically in FIG. 3 by the variable resistance symbol 60. Incidentally, when reference is made to a fixed resistance or resistor, this may refer to more than one resistor connected in series, for example.

As discussed in the present specification, it has been determined that by using a balanced square wave excitation for the circuit of FIG. 3 and by having the resistance between the the probes in parallel with resistors 54 and 56 of the Wheatstone bridge, both long term drift and also short term fluctuations may be minimized and the output of the conductivity sensor may be stabilized.

Figure 4:
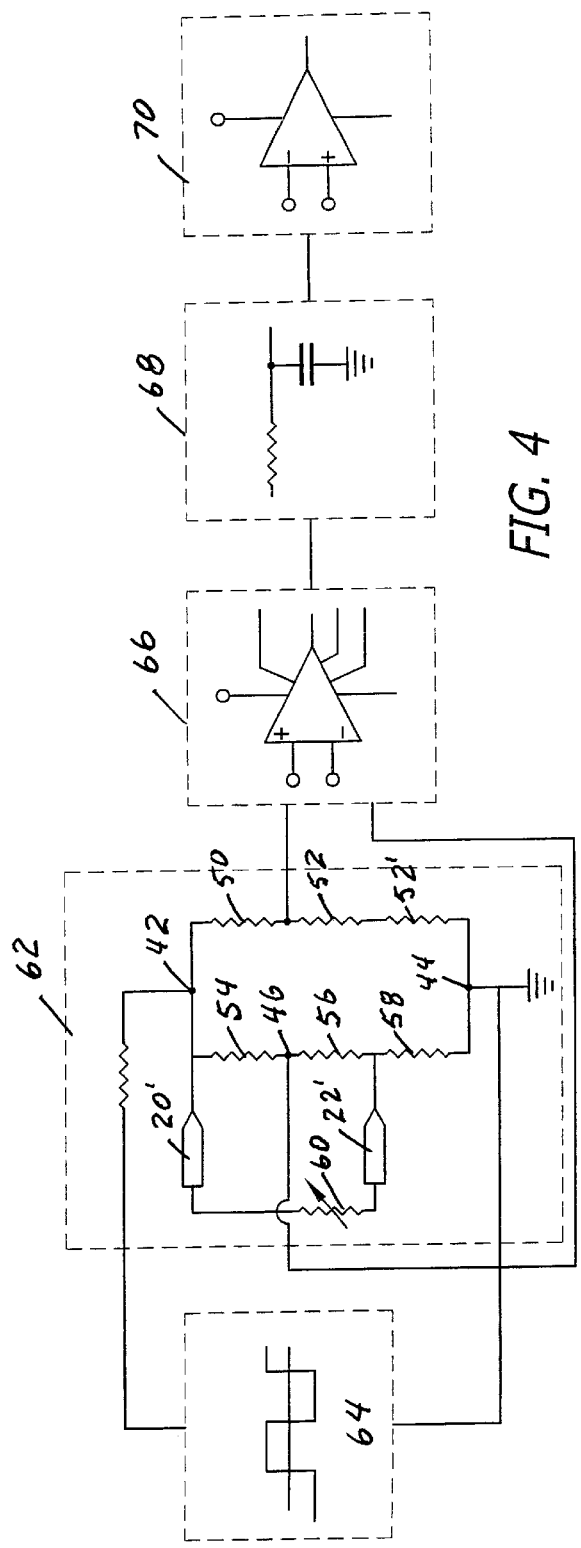
FIG. 4 is a schematic block circuit diagram.

Referring now to FIG. 4 of the drawings, the modified Wheatstone bridge of FIG. 3 is included within the dashed line block 62. The balanced input excitation from the square wave generator 64 is also shown in FIG. 4. From the output of the Wheatstone bridge, signals are applied to the differential amplifier 66 which provides an output indicating the difference between the potentials from points 42 and 44, and the two output leads from the circuit 62. The low pass filter 68 is provided to eliminate any noise or switching transients which may arise from the processing of the square wave generator signals in the differential amplifier 66. From the low pass filter 68, the output signal is routed to the amplifier and offset control circuit 70.

Reference is now made to the data tabulated in Table number 1. Initially it may be noted that the data was prepared using a fluid having three different conductivities. Thus, as indicated on the left hand side of Table number 1, the three conditions of the water were, first, de-ionized water involving the three lower sets of data; secondly, using water having a conductivity of 100 micro siemens ($\mu$S); and finally the upper three rows of data were taken at a conductivity of the water equal to 200 micro siemens. In the first column of data the electrical circuit involved the probes being located to measure conductivity in parallel to the single resistor 54, as shown in FIG. 3. Note that there is a considerable variation or fluctuation in the signals, from 1.52 volts to 2.1 volts. This is a fluctuation of about 580 milivolts, or somewhat more than ½ volt. As can be appreciated, it would be difficult to get a precise reading of the conductivity of the fluid with such a very considerable fluctuation. In the second column, the probes now provide a resistance which is in parallel to the combination of resistor 54 and resistor 56, substantially as shown in FIG. 3 of the drawings. As can be seen from the table, the fluctuation in reading has now been reduced substantially to 320 milivolts, as compared with the fluctuation of 580 milivolts shown in the first column for this conductivity level. Now, proceeding to the right hand side of the table, the third and fourth columns both involve excitation by balanced alternating current, or more specifically, by a square wave source as indicated at reference numeral 64 in FIG. 4 of the drawings. With the probes placing the variable resistance of the fluid in parallel with only resistor 54, as shown in the third column of Table 1, the fluctuation is 11 milivolts. However, when the probes are placed so the that resistance of the fluid is in parallel with both resistors 54 and 56, the fluctuation is reduced to 5 milivolts, which is acceptable under the circumstances and produces an output voltage which may be readily interpreted. Proceeding down the table, it may be seen that in each case the square wave generator provides significant improvement, and locating the probes to place the fluid conductivity in parallel with the two resistors 54 and 56, produces a further stabilizing effect.

Figure 5:
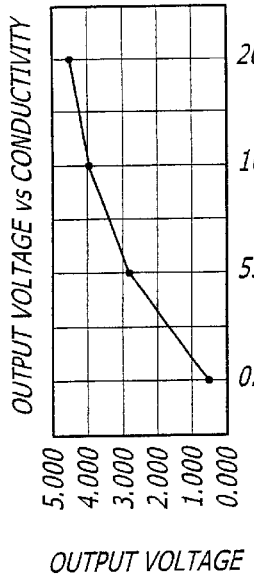
FIG. 5 is a plot of output voltage vs. conductivity for the overall system described in detail in the present specification.

Referring now to FIG. 5 of the drawings, a plot is shown of the output voltage against conductivity. With de-ionized water, the voltage output is approximately 0.5 volts; and the plot gradually increases until with conductivity of 200 micro siemens per centimeter, the voltage is approximately 4.5 volts.

Figure 6:
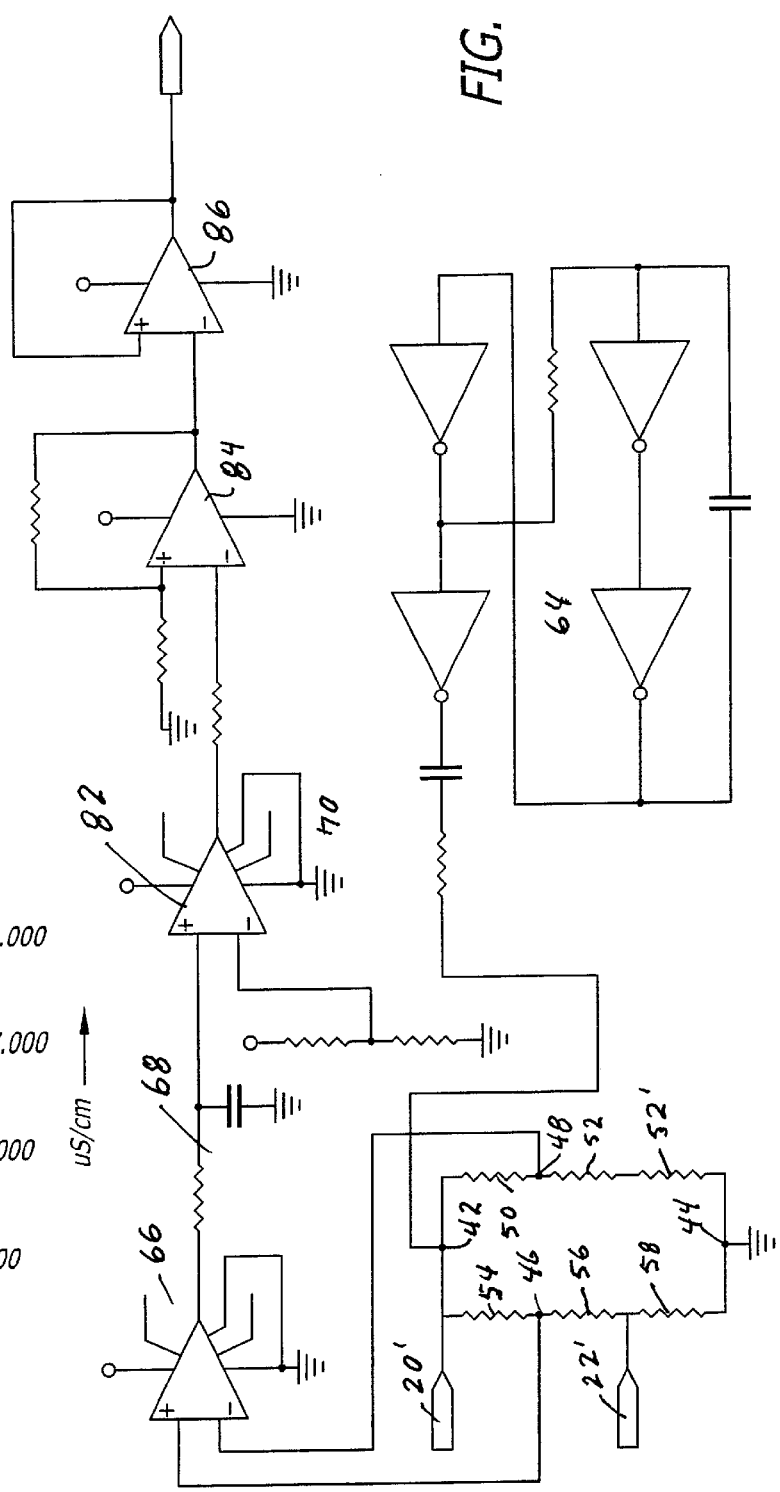
FIG. 6 is a more complete circuit diagram of one specific embodiment of the invention.

FIG. 6 of the drawings is a more complete circuit diagram showing the modified Wheatstone bridge circuit in the lower left of the figure, and with the square wave generator for excitation being shown at reference numeral 64 the lower right hand side of the drawings. The square wave frequency may be in the order of 10 or 20 kilohertz, and may have a 5 volt swing of from plus 2½ to minus 2½ volts, with the capacitor 65 blocking any net direct current flow. The differential amplifier is shown at reference numeral 68 with the resistive/capacitive low pass filter 68 immediately following circuit 66. Offset control and additional amplification are provided by the circuits 82, 84 and 86 as shown in FIG. 6. Finally, the output corresponding to the signals as shown in the plot of FIG. 5 are provided at output point 88. Incidentally, the circuit as shown in FIG. 6 of the drawings is located on the printed circuit boards 30 and 32 of FIG. 1, and the output signals as well as input power are provided at terminals 36 as shown in FIG. 1.

In conclusion, in the foregoing detailed description and in the associated drawings, one illustrative embodiment of the invention has been disclosed. It is to be understood, however, that various changes and modifications may be made without departing from the spirit and scope of the invention. Thus, by way of example and not of limitation, other physical enclosures and mounting arrangements or the two probes may be employed. For example, in the case of an open vessel containing fluid to be measured, the sensing system could be mounted on the upper lip of the vessel, with spaced plates extending down into the fluid. Also, the probes could have different shapes. In addition, the probe 20' could be connected to resistive arrangements providing the equivalent of a mid-point or intermediate point for resistor 54, with the probe or electrode 22' being located as indicated in FIG. 3. Accordingly, the invention is not limited to the precise form as shown and described in detail hereinabove.

TABLE 1

| | DC | | AC | |
|---|---|---|---|---|
| | $R_x//R_{54}$ | $R_x//R_{54} + R_{56}$ | $R_x//R_{54}$ | $R_x//R_{54} + R_{56}$ |
| | 200 μs | | | |
| Vmax | 2.1 (v) | 2.7 (v) | 1.588 (v) | 1.231 (v) |
| Vmin | 1.52 (v) | 1.85 (v) | 1.599 (v) | 1.236 (v) |
| ΔV | 580 (mv) | 320 (mv) | 11 (mv) | 5 (mv) |
| | 100 μs | | | |
| Vmax | 1.55 (v) | 1.53 (v) | 1.3825 (v) | 0.9754 (v) |
| Vmin | 1.48 (v) | 1.49 (v) | 1.3813 (v) | 0.9749 (v) |
| ΔV | 70 (mv) | 40 (mv) | 1.2 (mv) | 0.5 (mv) |
| | De-Ionized Water | | | |
| Vmax | 0.5051 (v) | 0.4989 (v) | .17980 (v) | .17964 (v) |
| Vmin | 0.5046 (v) | 0.4669 (v) | .17961 (v) | 0.17946 (v) |
| ΔV | 0.5 (mv) | 0.32 (mv) | 0.19 (mv) | 0.18 (mv) |

What is claimed is:

1. A stabilized fluid conductivity measurement system comprising:
   a threaded metal housing for mounting into a container for fluids, said fluid having conductivity to be measured; said housing having an inner portion to extend into the fluid, and an outer portion;
   first and second probes or electrodes;
   insulative support arrangements mounted on the inner portion of said housing to support said probes or electrodes in spaced relationship to each other;
   circuitry coupled to said probes mounted within the outer portion of said housing;
   said circuitry including a modified Wheatstone bridge circuit having first and second input excitation terminals and first and second output terminals;
   a source of balanced square wave signals coupled to said input excitation terminals;
   an additional fixed resistance coupled between said first input and said first output terminals, and another fixed resistance coupled between said first output terminal and said second input terminal;
   fixed resistance coupled between said first input terminal and said second output terminal;
   resistive circuitry having an intermediate tap, mounted between said second output terminal and said second input terminal;
   the first of said probes being connected to said tap; and
   the second of said probes being connected to said first input terminal.

2. A system as defined in claim 1 wherein one of said probes is mounted at the inner tip of said housing, and the other probe is ring shaped and mounted toward the threads of said housing from said tip.

3. A system as defined in claim 1 wherein said housing is generally cylindrical in shape, having a central axis, and wherein said probes are substantially symmetrically mounted with respect to said axis.

4. A system as defined in claims 1 further including an electrical connector mounted on the outer portion of said housing.

5. A system defined in claim 1 wherein said source of square wave signals is capacitively coupled to said input terminals.

6. A stabilized fluid conductivity measurement system comprising:
   a threaded metal housing for mounting into a container for fluids, said fluid having conductivity to be measured; said housing having an inner portion to extend into the fluid and an outer portion;
   first and second probes or electrodes;
   insulative support arrangements mounted on the inner portion of said housing to support said probes or electrodes in spaced relationship to each other;
   circuitry coupled to said probes mounted within the outer portion of said housing;
   said circuitry including a modified Wheatstone bridge circuit having first and second input excitation terminals and first and second output terminals;
   a source of balanced square wave signals coupled to said input excitation terminals;
   a fixed resistance coupled between said first input and said first output terminals, and another fixed resistance coupled between said first output terminal and said second input terminal;
   an additional fixed resistance coupled between said first input terminal and said second output terminal;
   resistive circuitry having an intermediate tap, mounted between said second output terminal and said second input terminal;
   the first of said probes being connected to said tap; and
   the second of said probes being connected to said modified Wheatstone bridge circuit between said first input terminal and said second output terminal, with resistance between said second probe connection point and said second output terminal.

7. A system as defined in claim 6 wherein one of said probes is mounted at the inner tip of said housing, and the other probe is ring shaped and mounted toward the threads of said housing from said tip.

8. A system as defined in claim 6 wherein said housing is generally cylindrical in shape, having a central axis, and wherein said probes are symmetrically mounted with respect to said axis.

9. A system as defined in claims 6 further including an electrical connector mounted on the outer portion of said housing.

10. A system defined in claim 6 wherein said source of square wave signals is capacitively coupled to said input terminals.

11. A stabilized fluid conductivity measurement system comprising:
    first and second probes or electrodes;
    insulative support arrangements mounted to support said probes or electrodes in spaced relationship to each other within the fluid to be measured;
    circuitry coupled to said probes, said circuitry including a modified Wheatstone bridge circuit having first and second input excitation terminals and first and second output terminals;
    a source of balanced square wave signals coupled to said input excitation terminals;
    an additional a fixed resistance coupled between said first input and said first output terminals, and another fixed resistance coupled between said first output terminal and said second input terminal;

fixed resistance coupled between said first input terminal and said second output terminal;

resistive circuitry having an intermediate tap, mounted between said second output terminal and said second input terminal;

the first of said probes being connected to said tap; and the second of said probes being connected to said first input terminal.

12. A system as defined in claim 11 wherein said system includes a threaded housing and wherein one of said probes is mounted at the inner tip of said housing, and the other probe is ring shaped and mounted toward the threads of said housing from said tip.

13. A system as defined in claim 12 wherein said housing is generally cylindrical in shape, having a central axis, and wherein said probes are substantially symmetrically mounted with respect to said axis.

14. A system as defined in claims 12 further including an electrical connector mounted on the outer portion of said housing.

15. A system defined in claim 11 wherein said source of square wave signals is capacitively coupled to said input terminals.

16. A stabilized fluid conductivity measurement system comprising:

first and second probes or electrodes;

support arrangements to support said probes or electrodes in spaced relationship to each other;

circuitry coupled to said probes, said circuitry including a modified Wheatstone bridge circuit having first and second input excitation terminals and first and second output terminals;

a source of balanced square wave signals coupled to said input excitation terminals;

a fixed resistance coupled between said first input and said first output terminals, and another fixed resistance coupled between said first output terminal and said second input terminal;

an additional fixed resistance coupled between said first input terminal and said second output terminal;

resistive circuitry having an intermediate tap, mounted between said second output terminal and said second input terminal;

the first of said probes being connected to said tap; and the second of said probes being connected to said modified Wheatstone bridge circuit between said first input terminal and said second output terminal, with resistance between said second probe connection point and said second output terminal.

17. A system as defined in claim 16 wherein said system includes a threaded housing and wherein one of said probes is mounted at the inner tip of said housing, and the other probe is ring shaped and mounted toward the threads of said housing from said tip.

18. A system as defined in claim 17 wherein said housing is generally cylindrical in shape, having a central axis, and wherein said probes are substantially symmetrically mounted with respect to said axis.

19. A system as defined in claims 17 further including an electrical connector mounted on the outer portion of said housing.

20. A system defined in claim 16 wherein said source of square wave signals is capacitively coupled to said input terminals.

* * * * *